United States Patent [19]

Richter et al.

[11] Patent Number: 4,614,785

[45] Date of Patent: Sep. 30, 1986

[54] PROCESS FOR THE PRODUCTION OF OLIGOMERIC POLYISOCYANATES AND THEIR USE IN THE PRODUCTION OF POLYURETHANE PLASTICS

[75] Inventors: Roland Richter, Cologne; Hanns P. Müller, Odenthal; Werner Kubitza, Leverkusen; Theodor Engbert, Dormagen; Gerhard Mennicken, Leverkusen, all of Fed. Rep. of Germany

[73] Assignee: Bayer Aktiengesellschaft, Leverkusen, Fed. Rep. of Germany

[21] Appl. No.: 765,472

[22] Filed: Aug. 14, 1985

[30] Foreign Application Priority Data

Aug. 31, 1984 [DE] Fed. Rep. of Germany ....... 3432081

[51] Int. Cl.⁴ .............................................. C08G 18/80
[52] U.S. Cl. ...................................... 528/45; 540/202; 528/67; 528/73; 544/193
[58] Field of Search ............................. 528/45, 67, 73; 260/239 AR; 544/193

[56] References Cited

U.S. PATENT DOCUMENTS

| | | | |
|---|---|---|---|
| 3,290,288 | 12/1966 | Oertel et al. | 260/239 |
| 3,645,979 | 2/1972 | Liebsch et al. | 260/77.5 |
| 4,113,945 | 9/1978 | Kauffman | 544/193 |
| 4,388,245 | 6/1983 | Ueyanagi et al. | 260/239 A |
| 4,476,054 | 10/1984 | Disteldorf | 260/239 |
| 4,520,186 | 5/1985 | Hess et al. | 260/239 A |

FOREIGN PATENT DOCUMENTS 1670720 1/1971 Fed. Rep. of Germany .
3227779 1/1984 Fed. Rep. of Germany .
1244416 9/1971 United Kingdom .

OTHER PUBLICATIONS

A. Darkas and G. A. Mills, Adv. Catal. 13, (1962), pp. 393 et seq.

*Primary Examiner*—Maurice J. Welsh
*Attorney, Agent, or Firm*—Gene Harsh; Joseph C. Gil; Thomas W. Roy

[57] ABSTRACT

The present invention relates to a process for the production of oligomeric polyisocyanates by the dimerization or trimerization of a portion of the isocyanate groups in organic polyisocyanates in the presence of tertiary phosphines or in the presence of a peralkylated phosphorus acid triamides as catalyst, followed by termination of the dimerization and/or trimerization reaction at the required degree of oligomerization by the addition of a catalyst poison, characterized in that a sulfonyl isocyanate is used as the catalyst poison.

The present invention also relates to the use of the oligomeric polyisocyanates obtained by this process, optionally in admixture with unreacted starting polyisocyanate or optionally blocked by blocking agents for isocyanate groups, as the polyisocyanate component in the production of polyurethane plastics.

20 Claims, No Drawings

PROCESS FOR THE PRODUCTION OF OLIGOMERIC POLYISOCYANATES AND THEIR USE IN THE PRODUCTION OF POLYURETHANE PLASTICS

BACKGROUND OF THE INVENTION

1. Field of the Invention

This invention relates to a new process for the production of oligomeric polyisocyanates containing uretdione and/or isocyanurate structural units by the dimerization and/or trimerization of a portion of the isocyanate groups in organic polyisocyanates using tertiary phosphines or peralkylated phosphorus acid triamides as dimerization and/or trimerization catalyst, followed by termination of the dimerization and/or trimerization reaction by the addition of catalyst poison, sulfonyl isocyanates, optionally in combination with organic acid chlorides, being used as the catalyst poison, and to the use of the products obtained by this process in the production of polyurethane plastics.

2. Description of the Prior Art

The production of isocyanato-uretdiones or isocyanato-isocyanurates or mixtures thereof by the dimerization and/or trimerization of a portion of the isocyanate groups in organic polyisocyanates using aliphatic, araliphatic or mixed aliphatic-aromatic tertiary phosphines or peralkylated phosphorus acid triamides as catalyst is already known. The question of whether dimerization products predominantly containing uretdione groups or trimerization products predominantly containing isocyanurate groups are formed in this reaction depends to a large extent upon the degree of conversion and upon the temperature profile (cf. A Farkas and G. A. Mills, Adv. Catal. 13 (1962) pages 393 et seq).

Generally, it may be said that with increasing temperature and increasing reaction time, the reaction proceeds via the uretdione preliminary stage to the isocyanurate trimers predominantly containing one isocyanurate ring and, ultimately, to isocyanurate polyisocyanates which, in addition to monoisocyanurates, also contain homologs with more than one isocyanurate ring. Both the predominantly pure dimerization products and mixtures thereof with the trimerization products and also the predominantly pure trimerization products represent valuable starting materials for the production of polyurethane plastics, the degree of dimerization or trimerization being adapted to the particular application envisaged in the production of oligomeric polyisocyanates. In either case, however, it is essential, if production is to be carried out reproducibly on an industrial scale, to terminate the dimerization and/or trimerization reaction precisely and quickly at a predetermined point.

In order cleanly to terminate the reaction at the desired conversion level, compounds which are intended to neutralize the effect of the catalyst are frequently added to the reaction mixture.

According to DE-OS No. 1,670,667 and to DE-OS No. 1,670,720, these compounds are preferably alkylating agents such as dimethyl sulfate, methyl iodide or toluene sulfonic acid esters, and acylating agents such as carboxylic acid chlorides and carbamic acid chlorides. However, these compounds are attended by the disadvantage that they do not neutralize the effect of the catalyst instantly and completely. Instead reheating is generally necessary (thus, an increase in temperature to 80° C. is proposed in DE-OS No. 1,670,720), with the result that the polymerization reaction cannot be cleanly terminated.

According to DE-AS No. 1,954,093, sulfur is suitable for deactivating tertiary phosphine catalysts. Although sulfur has the advantage of deactivating the tertiary phosphine catalysts spontaneously and quickly, the phosphine sulfide formed is generally a readily volatile compound. Thus, when the unreacted starting polyisocyanate is removed from the reaction mixture by distillation, the phosphine sulfide distills off with it and contaminates the distillate. Since the distillate is normally recycled, the amount of phosphine sulfide accumulates to an increasing extent.

In the processes according to U.S. Pat. No. 3,290,288, DE-OS No. 3,030,513 and DE-OS No. 3,227,779, peralkylated phosphorus acid triamides, such as tris-(dimethylamino)-phosphine, are preferably used as catalysts. At the same time, it is proposed to subject the reaction product to distillation on reaching the required conversion level without deactivating the catalyst. Although the catalysts mentioned accelerate above all dimerization, but not trimerization, it is nevertheless possible when this procedure is adopted for uncontrollable quantities of trimers to be formed from the uretdiones and excess starting polyisocyanates due to the high distillation temperature. This is why DE-OS No. 3,030,513 and DE-OS No. 3,227,779 recommend using only sterically hindered (cyclo) aliphatic starting diisocyanates. Thus, it must be assumed that the process according to those prior publications only enables dimeric diisocyanates to be reproducibly obtained where special starting diisocyanates are used. In addition, it is important to point out that the distillate which contains the active catalyst cannot be subjected to prolonged intermediate storage before it is reused because, in that case, it would undergo polymerization throughout and would thus become unusable.

Accordingly, the object of the invention is to provide a new process for dimerizing and/or trimerizing organic polyisocyanates using the state-of-the-art catalysts mentioned in the foregoing, which enables the reaction to be stopped satisfactorily and immediately at the particular conversion level required without being attended by any of the disadvantages of the prior art cited above.

This object is achieved by the process according to the invention which is described in detail hereinafter.

SUMMARY OF THE INVENTION

The present invention relates to a process for the production of oligomeric polyisocyanates by the dimerization or trimerization of a portion of the isocyanate groups in organic polyisocyanates in the presence of tertiary phosphines or in the presence of a peralkylated phosphorus acid triamides as catalyst, followed by termination of the dimerization and/or trimerization reaction at the required degree of oligomerization by the addition of a catalyst poison, characterized in that a sulfonyl isocyanate is used as the catalyst poison.

The present invention also relates to the use of the oligomeric polyisocyanates obtained by this process, optionally in admixture with unreacted starting polyisocyanate or optionally blocked by blocking agents for isocyanate groups, as the polyisocyanate component in the production of polyurethane plastics.

DETAILED DESCRIPTION OF THE INVENTION

The suitability of the sulfonyl isocyanates used as catalyst poison in accordance with the invention for deactivating the catalysts used in the process according to the invention, particularly the tertiary phosphines, was surprising because it was apparent from the relevant literature that the adducts in question are highly labile compounds. Thus, only triphenyl phosphine reacts with the highly reactive fluorosulfonyl isocyanate (H. Hoffmann, H. Förster and G. Tor-Poghossian, Mh. Chem., Vol. 100 (1969), page 312) and with sulfonyl diisocyanate (R. Appel and H. Rittersbacher, Chem. Ber. 97 (1964), pages 852 et seq) to form a defined adduct; whereas, the reaction with chlorosulfonyl isocyanate is not a uniform reaction. Tosyl isocyanate can only be reacted with tert.-butyl methyl phenyl phosphine at −78° C. to form a 1:1-adduct which is unstable at room temperature (C. R. Hall and D. J. H. Smith, J. C. S. Perkin II (1977), pages 1381 to 1382).

Any organic polyisocyanates containing aliphatically, cycloaliphatically, aromatically and/or araliphatically bound isocyanate groups may be used in the process according to the invention. Organic diisocyanates containing aliphatically, cycloaliphatically or aromatically bound isocyanate groups and having a molecular weight in the range from 168 to 300 are preferably used. Mixtures of these polyisocyanates and diisocyanates may of course also be used.

The polyisocyanates suitable for use as starting materials include, for example, those corresponding to the following formula $$Q(NCO)_n$$

in which n is an integer of from 2 to 4, preferably 2, and

Q represents an aliphatic hydrocarbon radical containing 2 to 18, preferably 6 to 10 carbon atoms; a cycloaliphatic hydrocarbon radical containing 4 to 15, preferably 5 to 10 carbon atoms; an aromatic hydrocarbon radical containing 6 to 15, preferably 6 to 13 carbon atoms: or an araliphatic hydrocarbon radical containing 8 to 15, preferably 8 to 13 carbon atoms.

Examples of these polyisocyanates include ethylene diisocyanate, 1,4-tetramethylene diisocyanate, hexamethylene diisocyanate, 1,12-dodecamethylene diisocyanate, cyclobutane-1,3-diisocyanate, cyclohexane-1,3- and -1,4-diisocyanate, 1-isocyanato-3,3,5-trimethyl-5-isocyanato-methyl cyclohexane (isophorone diisocyanate), hexahydro-1,3- and/or -1,4-phenylene diisocyanate, perhydro-2,4'- and/or -4,4'-diphenylmethane diisocyanate, 1,3- and 1,4-phenylene diisocyanate, 2,4- and 2,6-tolylene diisocyanate and mixtures of these isomers, diphenylmethane-2,4'- and/or -4,4'-diisocyanate, naphthylene-1,5-diisocyanate, 1-methyl-1-isocyanato-4-(1-isocyanato-but-3-yl)-cyclohexane, 1-methyl-1-isocyanato-4-isocyanatomethyl cyclohexane, 2,6-diisocyanato-n-hexanic acid methyl ester ("lysine methyl ester diisocyanate"), triphenylmethane-4,4',4''-triisocyanate or polyphenyl-polymethylene polyisocyanates of the type obtained by phosgenating anilineformaldehyde condensates.

Preferred starting materials for the process according to the invention include hexamethylene diisocyanate, isophorone diisocyanate, perhydro-2,4'- and -4,4'-diisocyanatodiphenylmethane, 2,4-diisocyanatotoluene and technical mixtures thereof with up to about 35% by weight (based on the total weight) of 2,6-diisocyanatotoluene, 4,4'-diisocyanatodiphenylmethane and mixtures thereof with 2,4'-diisocyanatodiphenylmethane containing up to 60% by weight (based on the mixture as a whole) of 2,4'-isomers and mixtures of the above-mentioned diisocyanates, particularly mixtures of aromatic diisocyanates of the above-mentioned type with cycloaliphatic and/or aliphatic diisocyanates of the above-mentioned type.

The catalysts used in the process according to the invention are tertiary phosphines or peralkylated phosphorus acid triamides. Mixtures of tertiary phosphines and peralkylated phosphorus acid triamides may of course also be used, although this is less preferred. Suitable tertiary phosphines are, in particular, aliphatic, araliphatic or mixed aliphatic-aromatic phosphines having a molecular weight of 76 to about 500, i.e., compounds which correspond to the definition and which have the general formula

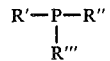

in which R', R'' and R''' may be the same or different and represent alkyl groups containing 1 to 10, preferably 2 to 8 carbon atoms; aralkyl groups containing 7 to 10, preferably 7 carbon atoms; or aryl groups containing 6 to 10, preferably 6 carbon atoms, with the proviso that at most one of the radicals represents an aryl group and preferably at least one of the radicals represents an alkyl group. When two of the radicals are aliphatic and form with the phosphorus atom a 4- to 6-membered ring containing phosphorus as heteroatom, the third of the radicals mentioned represents an alkyl group containing from 1 to 4 carbon atoms.

Examples of suitable tertiary phosphines are triethyl phosphine, dibutylethyl phosphine, tri-n-propyl phosphine, triisopropyl phosphine, tri-tert.-butyl phosphine, tribenzyl phosphine, benzyl dimethyl phosphine, dimethyl phenyl phosphine, tri-n-butyl phosphine, triisobutyl phosphine, triamyl phosphine, trioctyl phosphine or butyl-phosphacyclopentane. Tri(n-butyl)-phosphine is a particularly suitable catalyst for the process according to the invention.

Peralkylated phosphorus acid triamides suitable for use as catalysts are any organic compounds corresponding to the following general formula

in which the individual radicals R may be the same or different and preferably represent alkyl radicals containing 1 to 10, preferably 1 to 4 carbon atoms; aralkyl radicals containing 7 to 10, preferably 7 carbon atoms: or cycloalkyl radicals containing 4 to 10, preferably 6 carbon atoms. It can be seen from this definition of the radicals R that, in the context of the invention, the expression "peralkylated" may be broadly interpreted to mean that not only genuine alkyl radicals, but also cycloalkyl and aralkyl radicals may be considered as possible substituents for the nitrogen atom. However, the preferred peralkylated phosphorus acid triamides used as catalysts in accordance with the invention are those corresponding to the above general formula in which all the radicals R represents alkyl radicals containing from 1 to 4 carbon atoms, most preferably methyl radicals. The permethylated phosphorus acid triamide, i.e., tris-(dimethylamino)-phosphine, is the most preferred phosphorus acid triamide catalyst for use in the process according to the invention.

In the practical application of the process according to the invention, the catalysts are generally used in a quantity of about 0.01 to 2% by weight, based on the quantity of starting polyisocyanate. Where predominantly aromatic polyisocyanates are used as the starting polyisocyanate, the catalyst is preferably used in a quantity of about 0.01 to 0.1% by weight and, where predominantly cycloaliphatic or aliphatic polyisocyanates are used as the starting polyisocyanate, it is preferably used in a quantity of about 0.1 to 1% by weight, based in each case on the quantity of starting polyisocyanate.

The process according to the invention may be carried out in the presence or absence of solvents. When the process is carried out in the presence of solvents, the catalyst is preferably used in a slightly larger quantity within the ranges specified. Suitable inert organic solvents include, dioxane; esters such as methyl acetate, ethyl acetate, butyl acetate and methyl glycol acetate; ketones such as acetone, methyl ethyl ketone and cyclohexanone; and aromatic, aliphatic or even chlorinated hydrocarbons, except for carbon tetrachloride.

Sulfonyl isocyanates suitable for use in accordance with the invention are any inorganic or organic compounds which contain at least one structural unit corresponding to the following formula

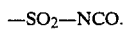
—SO$_2$—NCO.

Organic sulfonyl isocyanates are preferably used, while those containing aromatically-bound isocyanato-sulfonyl residues are particularly preferred. Processes for producing organic sulfonyl isocyanates of the type suitable for use in accordance with the invention and also their chemical behavior are comprehensively described by H. Ulrich in Chem. Rev. 65, pages 369–376, 1965. In addition, the production of aryl sulfonyl isocyanates is described in U.S. Pat. Nos. 2,666,787 and 3,484,466. According to the invention, it is possible to use aliphatic, cycloaliphatic and also aromatic mono- or polysulfonyl isocyanates, of which the following are mentioned by way of example: methyl sulfonyl isocyanate, butyl sulfonyl isocyanate, cyclohexyl sulfonyl isocyanate, perfluorooctyl sulfonyl isocyanate, phenyl sulfonyl isocyanate, p-toluene sulfonyl isocyanate, benzyl sulfonyl isocyanate, p-chlorophenyl sulfonyl isocyanate, m-nitrophenylsulfonyl isocyanate, 2,5-dimethyl phenyl sulfonyl isocyanate, p-fluorophenyl sulfonyl isocyanate, 2,5-dichlorophenyl sulfonyl isocyanate, 3,4-dichlorophenyl sulfonyl isocyanate, p-bromophenyl sulfonyl isocyanate, p-methoxyphenyl sulfonyl isocyanate, p-nitrophenyl sulfonyl isocyanate and o-nitrophenyl sulfonyl isocyanate; m-phenylene disulfonyl diisocyanate, p-phenylene disulfonyl diisocyanate, 4-methyl-m-phenylene disulfonyl diisocyanate, 2-chloro-p-phenylene disulfonyl diisocyanate, 5-chloro-m-phenylene disulfonyl diisocyanate, 1,5-naphthylene disulfonyl diisocyanate, 3-nitro-p-phenylene disulfonyl diisocyanate, 4-methoxy-m-phenylene disulfonyl diisocyanate, 2,5-furandiyl-bis-(methylene-sulfonyl)-diisocyanate, 4,4'-bis-phenylene disulfonyl diisocyanate, 2,2'-dichloro-4,4'-biphenylylene-disulfonyl diisocyanate, 3,3'-dimethoxy-4,4'-biphenylylene-disulfonyl diisocyanate, (methylene-di-p-phenylene)-disulfonyl diisocyanate, (methylene-di-3,3'-dimethoxy-p-phenylene)-disulfonyl diisocyanate, (methylene-di-3,3'-dimethyl-p-phenylene)-disulfonyl diisocyanate and 2-methyl-p-phenylene disulfonyl diisocyanate; also sulfonyl isocyanates containing free NCO-groups such as m-isocyanatophenyl sulfonyl isocyanate, p-isocyanatophenyl sulfonyl isocyanate, 3-isocyanato-p-tolyl sulfonyl isocyanate, 5-isocyanato-o-tolyl sulfonyl isocyanate, 3-isocyanato-4-methoxyphenyl sulfonyl isocyanate, 4-isocyanato-3-chlorophenyl sulfonyl isocyanate, 4'-isocyanato-4-biphenylyl sulfonyl isocyanate, 4'-isocyanato-2,2'-dichloro-4-biphenylyl sulfonyl isocyanate, 4'-isocyanato-3,3'-dimethoxy-4-biphenylyl sulfonyl isocyanate, α-(p-isocyanatophenyl)-p-tolyl sulfonyl isocyanate, α-(4-isocyanato-3-methoxyphenyl)-2-methoxy-p-tolyl sulfonyl isocyanate, α-(4-isocyanato-m-tolyl)-2,4-xylyl sulfonyl isocyanate and 5-isocyanato-1-naphthyl sulfonyl isocyanate; or containing free isothiocyanate groups such as p-isothiocyanatophenyl sulfonyl isocyanate, m-isothiocyanatophenyl sulfonyl isocyanate, 3-isothiocyanato-4-methoxy phenyl sulfonyl isocyanate and 4-isothiocyanato-3-methyl phenyl sulfonyl isocyanate.

It is preferred to use sulfonyl isocyanates wherein the —SO$_2$—NCO-group is directly attached to an aromatic radical. Phenyl sulfonyl isocyanate, p-chlorophenyl sulfonyl isocyanate and p-toluene sulfonyl isocyanate (tosyl isocyanate) are particularly preferred.

In addition to the organic sulfonyl isocyanates mentioned by way of example, it is also possible in accordance with the invention to use inorganic sulfonyl isocyanates such as chlorosulfonyl isocyanate or sulfonyl diisocyanate, of which the production is described in DE-PS No. 928,896 and in DE-PS No. 1,152,023. Oxy-sulfonyl isocyanates such as trimethyl silyloxy-sulfonyl isocyanate are also suitable.

In general, it is sufficient for terminating the reaction according to the invention to add one of the sulfonyl isocyanates mentioned by way of example to the reaction mixture in a quantity equivalent to the catalyst (molar ratio of —SO$_2$-NCO-groups to phosphorus atoms of the catalyst $\geq 1$), i.e., in the normal case where monofunctional phosphines and monofunctional sulfonyl isocyanates are used, the monofunctional sulfonyl isocyanates are added in at least equimolar quantities, based on the phosphine catalyst. However, if it is intended to remove unreacted monomeric starting material on completion of the reaction, for example by distillation, at least double the equivalent quantities, i.e , at least 2 moles of sulfonyl isocyanate groups per mole of phosphorus of the catalyst, are required to obtain a distillate completely free from phosphorus. This applies in particular where the preferred starting materials, such as for example, hexamethylene diisocyanate and-/or 4- or 2,6-diisocyanatotoluene, the preferred catalyst, tri-n-butyl phosphine, and the particularly preferred catalyst poison, p-toluene sulfonyl isocyanate (tosyl isocyanate), are used. This is surprising insofar as the adduct of tri-n-butyl phosphine and tosyl isocyanate which is produced in an inert medium is a 1:1-adduct irrespective of the molar ratios.

If, by contrast, chlorosulfonyl isocyanate or an oxy-sulfonyl isocyanate, such as trimethyl silyloxysulfonyl isocyanate is used as terminator, the molar quantity is entirely sufficient for obtaining a storable (NCO-stability) distillate.

Another possibility of freeing the products obtained by the process from unreacted, excess starting polyisocyanate by distillation and, at the same time, of obtaining a phosphine-free distillate is to use an organic acid chloride as another catalyst poison in addition to the sulfonyl isocyanate according to the invention. In that case, the sulfonyl isocyanates according to the invention are used in at least equivalent quantities, based on the phosphorus of the phosphine, together with an organic acid chloride, the two catalyst poisons being used in a total quantity, based on the phosphorus of the catalyst, of at least twice the equivalent quantity (molar ratio of sulfonyl isocyanate and acid chloride groups to P-atoms of the catalyst $\geq 2$). In this case, the acid chloride may be added together with or after the sulfonyl isocyanate.

Suitable organic acid chlorides are, in particular, carboxylic acid chlorides such as benzoyl chloride and isophthalic acid dichloride; carbamic acid chlorides such as phenyl carbamic acid chloride, tolyl-2,4-bis-carbamic acid chloride and hexyl carbamic acid chloride or, though less suitable, sulfonic acid chlorides such as benzene sulfonic acid chloride and p-toluene sulfonic acid chloride.

In cases where sulfonyl isocyanates are used which have boiling points in the region of or below the boiling point of the monomeric starting diisocyanate, it is possible that during the production of monomer-free products by the removal of excess, unreacted starting polyisocyanate by distillation, sulfonyl isocyanate may be present in the distillate on termination of the reaction. This undesirable possibility exists in particular when a larger than equivalent quantity of sulfonyl isocyanate or, in addition to an equivalent quantity of sulfonyl isocyanate, an organic acid chloride is used for termination. In both cases, the sulfonyl isocyanate present in the distillate may readily be destroyed by incorporating in the distillate a small quantity, i.e., a quantity at least equivalent to the distilled sulfonyl isocyanate, of a substance ("acceptor") which reacts with the highly reactive sulfonyl isocyanate to form inert, involatile products. When the distillate is subsequently reused in a fresh reaction mixture, the inert reaction product remains in the reaction product (distillation residue) without adversely affecting its properties. Where equivalent quantities of a sulfonyl isocyanate and, in addition, at least equivalent quantity of an organic acid chloride are used, it is also possible to add an "acceptor" for sulfonyl isocyanates to the reaction mixture after termination of the reaction and before removal of the excess starting polyisocyanate by distillation. In this case, too, the distillate does not contain any free sulfonyl isocyanate. There is no explanation for this surprising observation.

Suitable acceptors for sulfonyl isocyanates, particularly for the tosyl isocyanate, preferably used in accordance with the invention, include monohydric or polyhydric alcohols such as tert.-butanol, tetraethylene glycol, 2-ethyl-1,3-hexane diol, 3-methyl-1,5-pentane diol, 2,5-dimethyl-2,5-hexane diol or 2,5-hexane diol; tertiary amines such as N,N-dimethylbenzylamine or N,N-dimethylcyclohexylamine; aldehydes such as benzaldehyde, sulfoxides such as tetramethylene sulfoxide or dimethyl sulfoxide: or silanols such as trimethyl silanol.

The process according to the invention is carried out in known manner, as described, for example, in DE-AS No. 1,670,667, in DE-AS No. 1,954,093 or in DE-OS No. 3,227,779. In general, the starting polyisocyanate is kept at about 0° to 100° C. and preferably at about 20° to 60° C. in the presence of the catalyst until a conversion of about 5 to 70% and preferably about 20 to 60% is reached. In this connection, the term "conversion" is understood to mean the percentage of isocyanate groups in the starting polyisocyanate which are dimerized and/or trimerized during the reaction according to the invention. The conversion may readily be monitored from the reduction in the NCO-content of the reaction mixture. The question of whether predominantly uretdione-modified polyisocyanates (dimers) or predominantly isocyanurate-modified polyisocyanates (trimers) are formed in the process according to the invention depends both upon the conversion and upon the reaction temperature selected. In general, the reaction products according to the invention are mixtures of dimers and trimers of which the content of the above-mentioned modification products varies according to the above-mentioned parameters. When the starting polyisocyanates used form uretdiones which are insoluble in excess starting polyisocyanate, the optional, at least partial further reaction of the dimers to the trimers may be achieved by using a solvent of the type mentioned by way of example in the foregoing which prevent precipitation of the dimer. To terminate the reaction, the catalyst poison is added to the reaction mixture at the required NCO-content. The addition of the sulfonyl isocyanate results in immediate termination of the reaction, even at temperatures in the range of about 20° to 60° C. There is no need for reheating. On completion of the reaction and, optionally, after a brief period of stirring (10 to 60 minutes), unreacted monomeric starting isocyanate may be removed by any separation techniques such as distillation (particularly thin-layer distillation) or extraction. After any excess sulfonyl isocyanate has been destroyed by one of the acceptors mentioned by way of example in the foregoing, the recovered monomeric isocyanate may be reused without any loss of activity.

In addition to the reusability of the distillate, the products according to the invention have the advantage of being highly stable in storage, which is reflected in their constant viscosity and color and in their constant NCO-content. In particular, there is no danger when the above-mentioned catalyst poisons are used of the phosphine oxides readily formed during the reaction from tertiary phosphines and atmospheric oxygen leading (during working up) to the formation of secondary products (carbodiimides), because tosyl isocyanate for example reacts off with phosphine oxides (with elimination of $CO_2$) to form phosphine imines which have no catalytic activity (cf. C. R. Hall and D. J. H. Smith, J. C. S. Perkin II (1977), pages 1373 et seq).

The products obtained by the process according to the invention represent valuable starting materials for the production of polyurethane plastics and, in particular for the production of polyurethane lacquers and polyurethane adhesives by reaction with compounds containing isocyanate-reactive groups wherein at least a portion of the isocyanate-reactive groups are hydroxyl groups. Accordingly, they may be used in known manner substantially free from excess starting polyisocyanate, in the form of their solutions in excess starting polyisocyanates and, if desired, even blocked by blocking agents known per se.

The invention is further illustrated, but is not intended to be limited by the following examples in which all parts and percentages are by weight unless otherwise specified.

EXAMPLE 1

(Comparison of Various Catalyst Poisons with the Catalyst Poison According to the Invention)

In a suitable reaction vessel 200 part aliquots of hexamethylene diisocyanate were mixed with A: 1.0 part of tri-n-butyl phosphine
B: 1.0 part of tri-n-butyl phosphine and
  0.95 part of p-toluene sulfonic acid methyl ester
C: 1.0 part of tri-n-butyl phosphine and
  0.5 part of isophthalic acid chloride
D: 1.0 part of tri-n-butyl phosphine and
  1.0 part of dibutyl phosphate
E: 1.0 part of tri-n-butyl phosphine and
  0.75 part of 2-ethyl hexanic acid
F: 1.0 part of tri-n-butyl phosphine and
  0.16 part of elemental sulfur
G: 1.0 part of tri-n-butyl phosphine and
  0.98 part of p-toluene sulfonyl isocyanate (tosyl isocyanate), followed by stirring under nitrogen at 20° C.

The indicated quantities of the individual catalyst poisons were equivalent in every case to the quantity of phosphine. The conversion was determined by NCO-measurement after the following time intervals:

| NCO content after | 3 hours | 6 hours | 24 hours |
|---|---|---|---|
| A: | 44.5% | 42.4% | 32.2% |
| B: | 45.2% | 44.4% | 41.4% |
| C: | 49.1% | 48.8% | 48.4% |
| D: | 49.5% | 48.5% | 42.2% |
| E: | 44.9% | 42.2% | 33.6% |
| F: | 49.9% | 49.9% | 49.9% |
| G: | 49.8% | 49.8% | 49.8% |

This Example shows that neither alkylating agents (B), acylating agents (C) nor acidic compounds (D,E) show an adequate deactivating effect at 20° C.

EXAMPLE 2

(a) 1000 g (5.95 moles) of hexamethylene diisocyanate were introduced under nitrogen into a suitable reaction vessel followed by stirring at room temperature with 2.0 g (0.01 mole) of tri-n-butyl phosphine. After stirring for 18 hours the NCO-content had fallen to 40.5%. The reaction was terminated by the addition of 3.9 g (0.02 mole) of tosyl isocyanate. After stirring for 30 minutes, monomeric hexamethylene diisocyanate was distilled off in a thin layer evaporator at 160° C./0.15 mbar. 680 g of colorless distillate and 320 g of a monomer-free (<0.5%) yellowish sump product having an NCO-content of 22.7%, a mononuclear uretdione (molecular weight 336, as determined by gel chromatography) of 39% and a viscosity of 110 mPas (25° C.) were obtained. The NCO-content of the distillate was unchanged after storage for 1 month.

(b) After mixing with 320 g (1.9 moles) of fresh hexamethylene diisocyanate and stirring in 2.5 g (0.017 mole) of 2-ethyl-1,3-hexane diol, the distillate was repolymerized under the conditions described above, followed by working up. 315 g of yellowish polyisocyanate resin having an NCO-content of 22.2% and a viscosity of 108 mPas (25° C.) and 685 parts of colorless distillate which may be similarly recycled were obtained.

EXAMPLE 3

(Comparison)

The procedure was as in Example 2, except that 0.32 g (0.01 mole) of elemental sulfur was stirred in as terminator after the NCO-content has reached 40.5%. Working up in the same way gave a pale yellowish distillate with a tributyl phosphine sulfide content of 0.34% which doubled on further recycling and, in addition, adversely affected the color of the subsequent products (dark red-yellow discoloration).

EXAMPLE 4

The procedure was as in Example 2, except that only 2.0 g (0.01 mole) of tosyl isocyanate and, in addition, 1.0 g (0.005 mole) of isophthalic acid dichloride were stirred in after the NCO-content had reached 40.5%. Working up was then carried out in the same way as in Example 2.

The NCO-content of this distillate was again unchanged after storage for 1 month, showing that, with this procedure, too, no free phosphine was present in the distillate.

The products of Examples 2, 3 and 4 were tempered for 1 month at 50° C. in sealed containers. Thereafter, all three products had NCO-contents of 22.6 to 22.7% and were unchanged with regard to color and viscosity.

EXAMPLE 5

(a) 600 g (3.57 moles) of hexamethylene diisocyanate were introduced under nitrogen into a suitable reaction vessel, followed by stirring at room temperature with 1.5 g (0.007 mole) of tri-n-butyl phosphine. After stirring for 17 hours, the NCO-content had fallen to 41.1%. The reaction was terminated by the addition of 1.45 g (0.007 mole) of trimethyl silyloxy sulfonyl isocyanate. After stirring for 30 minutes, monomeric hexamethylene diisocyanate was distilled off in a thin layer evaporator at 160° C./0.15 mbar. 416 g of colorless distillate, the NCO-content of which remains completely constant during storage, and 184 g of a yellow polyisocyanate resin having an NCO-content of 22.5%, a free hexamethylene diisocyanate content of less than 0.4% and a viscosity of 117 mPas (25° C.) were obtained. The reaction product remained unchanged in its characteristics after storage for more than 6 months.

(b) Example 5a was repeated with the exception that 1.0 g (0.007 mole) of chlorosulfonyl isocyanate was used as terminator. A storable distillate and a polyisocyanate resin were again obtained, except that on this occasion the resin is dark yellow in color.

EXAMPLE 6

400 g (2.38 moles) of hexamethylene diisocyanate were introduced under dry nitrogen into a suitable reaction vessel. 4.0 g (0.025 mole) of freshly distilled hexamethyl phosphorus acid triamide were then added and the reaction mixture heated with thorough stirring at 60° C. After 45 minutes, the NCO-content was 39.4% and the ratio of uretdione to isocyanurate in the IR-spectrum was approximately 35:65 (band at 1770 $cm^{-1}$ to band at 1690 $cm^{-1}$). After storage for 20 days at 50° C., the NCO-content was unchanged, nor were any significant changes apparent with regard to color and the uretdione:isocyanurate ratio. Working up of the reaction mixture by thin-layer distillation at 160° C./0.15 mbar gave 152 g of a brownish-yellow residue having an NCO-content of 21.1% and a faintly yellow-tinged distillate (248 g) having an NCO-content of 49.6% which did not change on storage.

EXAMPLE 7

170 g (0.98 mole) of 2,4-tolylene diisocyanate and 330 g (1.96 moles) of hexamethylene diisocyanate were heated to 60° C. and polymerized in an inert gas atmosphere by the addition of 0.125 g (0.6 mmole) of tri-n-butyl phosphine. The temperature during the reaction phase was kept at around 60° C. by gentle cooling. When, after about 4.5 hours, an NCO-content of 36% was reached, the reaction was terminated by the addition of 0.25 g (1.3 mmoles) of tosyl isocyanate, followed by stirring for 30 minutes at 60° to 40° C. without further heating. Unreacted monomer mixture was then distilled off in a thin-layer evaporator (recirculation temperature 190° C., vacuum 0.15 mbar), giving 180 g of a brittle yellow solid resin having an NCO-content of 19.6% and, as distillate, 292 g of colorless monomer mixture, the NCO-content of which (49.4%) remained constant. The solid resin consisted essentially of isocyanurate units (aliphatic fraction approx. 40%).

EXAMPLE 8

(A) Adduct of tosyl isocyanate and tertiary phosphine.

3.0 g (14.9 mmoles) of tri-n-butyl phosphine were dissolved in 50 ml of absolute hexane and the resulting solution stirred with 2.93 g (14.9 mmoles) of tosyl isocyanate. A white crystalline solid product was precipitated, being isolated in the absence of moisture and dried.

Yield: 5.0 g (84% of the theoretical); melting point; 140° C. Structure:

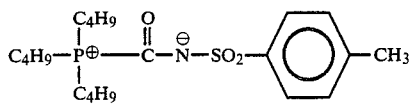

Analytical data:

IR: $V_{max.}$ (Nujol) 1620 cm$^{-1}$, 1440 cm$^{-1}$; $^{31}$p (81 MHz):

$\delta = 19.57$ ppm (rel. to ext. H$_3$PO$_4$); $^{13}$C(50.3 MHz):

$\delta = 162.28$ ppm d, $^1H_{C,P} = 103.6$ Hz (further signals below 141 ppm)

C$_{20}$H$_{34}$NO$_3$PS (399): Calc: S, 8.0; N, 3.51. Found: S, 8.5; N, 3.5.

(B) 500 g (2.98 moles) of hexamethylene diisocyanate were stirred for 17 hours at room temperature under dry nitrogen with 2.0 g (0.005 mole) of the adduct of tosyl isocyanate and tributyl phosphine (A), corresponding to 0.2% of tributyl phosphine. Thereafter, the NCO-content amounted to 49.3%. The solution was distilled at 160° C./0.15 mbar in a thin-layer evaporator. 498 g of colorless distillate having an NCO-content of 49.8% were obtained. After storage for 18 days at room temperature, the NCO-content had fallen to 45.5%, showing that phosphine was reformed under the distillation conditions.

(C) As in (B), 500 g (2.98 moles) of hexamethylene diisocyanate were stirred for 17 hours at room temperature with 2.0 g (0.005 mole) of adduct A and 1.0 g (0.005 mole) of tosyl isocyanate. Thereafter, the NCO-content amounted to 49.8%. The solution was distilled in the same way as described in (B), giving 496 g of colorless distillate having an NCO-content of 49.7%. This NCO-content was unchanged after storage for 18 days at room temperature.

Although the invention has been described in detail in the foregoing for the purpose of illustration, it is to be understood that such detail is solely for that purpose and that variations can be de therein by those skilled in the art without departing from the spirit and scope of the invention except as it may be limited by the claims.

What is claimed is:

1. A process for the production of an oligomeric polyisocyanate which comprises dimerizing and/or trimerizing a portion of the isocyanate groups of an organic polyisocyanate in the presence of a tertiary phosphine or a peralkylated phosphorus acid triamide as catalyst and terminating the dimerization and/or trimerization reaction at the desired degree of oligomerization by adding a sulfonyl isocyanate as the catalyst poison.

2. The process of claim 1 wherein said organic polyisocyanate is an organic diisocyanate having a molecular weight of 168 to about 300 and containing aliphatically, cycloaliphatically and/or aromatically bound isocyanate groups.

3. The process of claim 1 which comprises conducting said reaction at about 0° to 100° C. until about 5 to 70% of the isocyanate groups present in said organic polyisocyanate have been dimerized and/or trimerized and then terminating the reaction by the addition of said catalyst poison when that degree of conversion is reached.

4. The process of claim 1 wherein said sulfonyl isocyanate is used in at least an equivalent quantity, based on the catalyst.

5. The process of claim 2 wherein said sulfonyl isocyanate is used in at least an equivalent quantity, based on the catalyst.

6. The process of claim 1 wherein said sulfonyl isocyanate is used in at least twice the equivalent quantity, based on the catalyst.

7. The process of claim 2 wherein said sulfonyl isocyanate is used in at least twice the equivalent quantity, based on the catalyst.

8. The process of claim 1 wherein said sulfonyl isocyanate is used in at least an equivalent quantity, based on the catalyst, together with a quantity of an organic acid chloride such that in all at least 2 moles of sulfonyl isocyanate and acid chloride groups are available for each mole of phosphorus of the catalyst, which comprises adding the acid chloride at the same time as or after said sulfonyl isocyanate.

9. The process of claim 2 wherein said sulfonyl isocyanate is used in at least an equivalent quantity, based on the catalyst, together with a quantity of an organic acid chloride such that in all at least 2 moles of sulfonyl isocyanate and acid chloride groups are available for each mole of phosphorus of the catalyst, which comprises adding the acid chloride at the same time as or after said sulfonyl isocyanate.

10. The process of claim 1 wherein said sulfonyl isocyanate is an aromatic sulfonyl isocyanate.

11. The process of claim 2 wherein said sulfonyl isocyanate is an aromatic sulfonyl isocyanate.

12. The process of claim 4 wherein said sulfonyl isocyanate is an aromatic sulfonyl isocyanate.

13. The process of claim 1 wherein said sulfonyl isocyanate comprises tosyl isocyanate.

14. The process of claim 2 wherein said sulfonyl isocyanate comprises tosyl isocyanate.

15. The process of claim 4 wherein said sulfonyl isocyanate comprises tosyl isocyanate.

16. The process of claim 5 wherein said sulfonyl isocyanate comprises tosyl isocyanate.

17. The process of claim 6 wherein said sulfonyl isocyanate comprises tosyl isocyanate.

18. The process of claim 7 wherein said sulfonyl isocyanate comprises tosyl isocyanate.

19. The process of claim 3 which comprises removing the unreacted organic polyisocyanate from the reaction mixture by distillation after the reaction has been terminated.

20. A process for the production of a polyurethane which comprises
 (a) preparing an oligomeric polyisocyanate in accordance with claim 1, and
 (b) reacting said oligomeric polyisocyanate, optionally in blocked form, with a compound containing isocyanate-reactive groups wherein at least a portion of the isocyanate-reactive groups are hydroxyl groups.

* * * * *